US008089509B2

(12) United States Patent
Chatenever et al.

(10) Patent No.: US 8,089,509 B2
(45) Date of Patent: *Jan. 3, 2012

(54) PROGRAMMABLE CAMERA CONTROL UNIT WITH UPDATABLE PROGRAM

(75) Inventors: David Chatenever, Santa Barbara, CA (US); Marc R. Amling, Santa Barbara, CA (US)

(73) Assignee: Karl Storz Imaging, Inc., Goleta, CA (US)

( * ) Notice: Subject to any disclaimer, the term of this patent is extended or adjusted under 35 U.S.C. 154(b) by 1034 days.

This patent is subject to a terminal disclaimer.

(21) Appl. No.: 11/543,476

(22) Filed: Oct. 5, 2006

(65) Prior Publication Data
US 2007/0024717 A1    Feb. 1, 2007

Related U.S. Application Data

(63) Continuation-in-part of application No. 10/039,931, filed on Nov. 9, 2001, now Pat. No. 7,212,227.

(51) Int. Cl.
*H04N 5/225* (2006.01)
*A61B 1/04* (2006.01)
(52) U.S. Cl. ......................................... 348/72; 348/207.1
(58) Field of Classification Search .............. 348/72–76, 348/207.1, 211.4, 211.6, 211.9; 717/170
See application file for complete search history.

(56) References Cited

U.S. PATENT DOCUMENTS

| 4,816,909 A | 3/1989 | Kimura et al. |
| 5,584,292 A | 12/1996 | Cheung |
| 5,627,583 A | 5/1997 | Nakamura et al. ............. 348/72 |
| 5,754,422 A | 5/1998 | Lowles et al. ..................... 700/1 |
| 5,812,188 A | 9/1998 | Adair |
| 5,868,666 A | 2/1999 | Okada et al. .................. 600/118 |
| 5,871,439 A | 2/1999 | Takahashi et al. ............ 600/118 |
| 5,896,166 A | 4/1999 | D'Alfonso et al. ............ 348/72 |
| 6,184,922 B1 | 2/2001 | Saito et al. |
| 6,215,517 B1 | 4/2001 | Takahashi et al. ............. 348/72 |
| 6,249,311 B1 | 6/2001 | Rouse, Jr. et al. ............. 348/164 |
| 6,295,082 B1 | 9/2001 | Dowdy et al. .................. 348/72 |
| 6,313,868 B1 | 11/2001 | D'Alfonso et al. ............ 348/72 |
| 6,360,362 B1 | 3/2002 | Fichtner et al. ............... 717/168 |
| 6,452,629 B1 | 9/2002 | Aizawa et al. |
| 6,638,212 B1 | 10/2003 | Oshima ........................ 600/109 |

(Continued)

FOREIGN PATENT DOCUMENTS
EP    0994614 A2    4/2000
(Continued)

OTHER PUBLICATIONS

IEEE 100 The Authoritative Dictionary of IEEE Standard Terms, Seventh Edition, 2000, p. 874.*

(Continued)

*Primary Examiner* — Timothy J Henn
(74) *Attorney, Agent, or Firm* — St. Onge Steward Johnston & Reens LLC

(57) ABSTRACT

A video imaging system with a camera coupled to a camera control unit, the camera having a program stored thereon and the camera control unit comparing the program version stored on the camera with another version of the program such that the newer version of the program is loaded onto the camera control unit and camera control unit is programmed with the newer version of the program to enable the camera control unit to process image data received from the camera.

15 Claims, 5 Drawing Sheets

U.S. PATENT DOCUMENTS

| | | | |
|---|---|---|---|
| 6,707,490 B1 | 3/2004 | Kido et al. | 348/211.14 |
| 6,710,799 B2 | 3/2004 | Abnet et al. | 348/135 |
| 6,750,902 B1 | 6/2004 | Steinberg et al. | |
| 7,212,227 B2 * | 5/2007 | Amling et al. | 348/72 |
| 2002/0095501 A1 | 7/2002 | Chiloyan et al. | 709/227 |
| 2003/0220947 A1 | 11/2003 | Doui | |
| 2004/0141054 A1 | 7/2004 | Mochida et al. | |
| 2004/0201743 A1 | 10/2004 | Amling et al. | |
| 2004/0218065 A1 | 11/2004 | Schinner | |
| 2005/0278461 A1 * | 12/2005 | Ohta | 710/8 |
| 2006/0055793 A1 | 3/2006 | Adler et al. | |
| 2006/0092312 A1 | 5/2006 | Tanaka | |
| 2007/0124459 A1 * | 5/2007 | Kasama | 709/224 |
| 2008/0117442 A1 | 5/2008 | Kosaka et al. | |

FOREIGN PATENT DOCUMENTS

| | | |
|---|---|---|
| EP | 1311117 A2 * | 5/2003 |
| EP | 1679030 A1 | 7/2006 |
| EP | 1909490 A2 | 4/2008 |
| JP | 11047089 A | 2/1999 |
| JP | 2000165960 A | 6/2000 |
| JP | 2000175089 | 6/2000 |
| JP | 2001099627 | 4/2001 |
| JP | 2003288211 A | 10/2003 |
| JP | 2004007368 A | 1/2004 |
| JP | 2006243997 A | 9/2006 |

OTHER PUBLICATIONS

Description of "software", The IEEE Standard Dictionary of Electrical and Electronics Terms, Sixth Edition, 1996, p. 1006.

European Search Report; Jan. 20, 2006; 3 pages.

Anonymous: "Datacube introduces world•s highest performance CameraLink frame grabber" Internet Article, •Online! Oct. 30, 2001, XP002362612 Retrieved from the Internet: URL:www.datacube.com/downloads/MaxRevProdIntro.htm•retrieved on Jan. 12, 2006! *the whole document*.

Anonymous: "MaxRevolution datasheet" Internet Article, •Online! pp. 1-2, Retrieved from the Internet: URL:http://www.datacube.com/downloads/Datasheet_MaxRevolution.pdf• retrieved on Jan. 12, 2006 * the whole document*.

European Search Report; EP 09 17 5038; Jan. 25, 2010; 9 pages.

European Search Report, EP07019564, Sep. 8, 2008, 2 Pages.

* cited by examiner

PROGRAMMABLE CAMERA CONTROL UNIT WITH UPDATABLE PROGRAM

CROSS-REFERENCE TO RELATED APPLICATIONS

This application is a continuation-in-part of 10/039,931 filed Nov. 9, 2001, now U.S. Pat. No. 7,212,227 is-sued May 1, 2007.

FIELD OF THE INVENTION

The invention relates to a camera control unit capable of processing a video signal from many different types of video cameras and, more particularly, the invention relates to programming and/or configuring the camera control unit with the newest available version of a program(s).

BACKGROUND OF THE INVENTION

Cameras and camera control units ("control unit") are generally used together to capture and process images. Cameras may include charge couple devices ("CCD") and they typically capture, or pick up, images and send an image signal to the control unit. This image signal may be sent to the control unit via a cable or it may be sent through a wireless communication. Upon receiving the image signal, the control unit processes it into a displayable image, such as an image on a monitor or television. The control unit also sends commands to the CCD in order to adjust camera settings.

A camera and control unit may be connected to one another in a single unit or may be separate from one another, being connected, for example, by a cable for transmitting data. A camera may be remotely held away from a control unit in situations where space is limited or mobility is desired, such as during endoscopic surgery.

Known control units typically control a single type of camera by receiving and processing the image captured by the CCD. Once an image is captured and a signal is sent by the camera to the control unit, the control unit processes the signal into a displayable image, whereby a user can view the image captured by the CCD. A control unit generally operates as the brain of the camera and commands the camera to adjust color balance, light, focal distance, resolution, zoom, focus, shading, and other optical characteristics. A single camera may obtain image signals from a plurality of CCDs, including different types of CCDs or from a single CCD. It is this variability of cameras which has, in essence, meant that each camera has its own control unit.

Traditionally, control units were compatible with a limited number of CCDs because the control units' hardware, through which commands were sent and image signals were received, was difficult to configure to communicate with the many different types of cameras in the market. For example, different cameras and/or CCDs may have varying electronic requirements/connections in order to function properly. CCDs may be analog and send analog signals to the CCU whereas other CCDs may be digital and send digital signals to the CCU. Also, some CCDs may be designated to pick up certain colors such as red or green while others pick up blue. Further, depending upon the manufacturer, there may be differences among CCDs and, in particular, when some, but not all, CCDs are replaced. In addition, as changes and improvements are made to the cameras, a control unit's hardware, which was configured to be compatible with older cameras, may become incompatible and may need to be upgraded as well.

Moreover, control units are generally made to be used with cameras currently in existence and are not designed to future camera configurations not yet known. This is because CCDs send image signals to the control units and, in order to process these signals, control units' technologies need to be compatible with those of the cameras. Hence, control units are typically not made to be compatible with future camera technologies and the differences among older and newer cameras may contribute toward compatibility problems between control units and cameras and, therefore, control units are generally compatible with a selected number of cameras.

Because they were compatible with limited quantities of cameras, control units were typically discarded in favor of control units that were made concurrently and/or compatible with particular cameras. Consequently, control units have become an added expense often associated when changing CCDs or cameras. This expense is then possibly passed onto consumers. Further, it is typically desired for cameras to be improved because there is a demand from consumers to have the latest technology and advancement in equipment.

What is desired, therefore, is to provide a control unit that is capable of maintaining compatibility with any type of camera. What is also desired is to provide a control unit whose hardware can be upgraded or configured to maintain capability with any type of camera.

SUMMARY OF THE INVENTION

Accordingly, it is an object of the invention to provide a programmable camera control unit that is capable of maintaining compatibility with any type of camera.

It is also an object to provide configurable hardware for a camera control unit.

It is still further desired to provide a configurable camera control unit that may be programmed with the latest version of software available for the application.

These and other objects of the invention are achieved by providing a video imaging system including a camera for transmitting image data to a camera control unit, a camera control unit for receiving and processing the image data into a displayable format, and software executing on the camera control unit for determining when the camera is in communication with the camera control unit and for retrieving a program or multiple programs stored on a storage device. The retrieved program(s) execute on the camera control unit for enabling the camera control unit to process the image data.

The video imaging system may further include a field programmable gate array (e.g. a configurable hardware device) for configuring the control unit using the program retrieved from the storage device. More specifically, the program configures the field programmable gate array to enable the camera to be compatible with the camera with which it is in communication. Alternatively, the configurable control unit may comprise a microprocessor or a Digital Signal Processor (DSP) (e.g. a soft configurable device) that may be programmed depending upon the camera attached thereto.

The storage device is any type of storage medium accessible by the control unit. It may be an internal, external, or removable drive and may also include a remote location, such as an Internet location. The storage device may also be located within the camera and/or camera control unit. It is further contemplated that multiple storage devices and/or locations may be used to provide the latest version of software and/or programs for the configurable control unit.

The program(s) further enable the control unit to issue commands to the camera in order to regulate the camera's optical characteristics, such as focal distance, resolution, light balance, or color. In return, the camera sends confirmation to the control unit that the commands were received and/or will adjust in response to the given commands.

The video imaging system may also include a further storage device for storing processed image data. Instead of displaying image data from a camera, the control unit may send the processed image data to a storage device, such as an internal, external, or removable drive. This may be for instances where viewing the processed image data at a later time or saving it is desired.

In one embodiment, a video imaging system may be provided including a field programmable gate array having a first section for requesting the program and a programmable second section. The video imaging system may also include a microprocessor for executing the program, whereby the program configures the programmable second section and enables the control unit to process image data.

Further, in configuring the programmable second section, the program may overwrite an existing program. The first section of the field programmable gate array may also be permanently configured for requesting and/or loading programs for configuring the control unit.

In a further embodiment, an endoscopic imaging system may be provided including an endoscope for capturing and transmitting image data. The endoscope may further include a storage device for storing the program for configuring the programmable second section of the field programmable gate array. In addition, the endoscope may adjust optical characteristics in response to commands from the control unit. The endoscope may also send confirmation to the control unit when the commands are received and/or carried out.

In another aspect, the invention includes a method for providing a video imaging system. The method includes determining when a camera is in communication with a camera control unit, accessing a storage device, retrieving a program stored on the storage device, executing the program on the control unit, and enabling the control unit to process image data.

In one advantageous embodiment, a video imaging system is provided comprising a camera for generating image data. The camera includes a first storage device positioned on the camera and a program stored on the storage device the program comprising a first version of the program. The system further comprises a camera control unit coupled to the camera and receiving the image data. The camera control unit includes a processor and at least one programmable device. The system still further comprises a second storage device accessible by the processor, the second storage device having a second version of the program stored thereon. The system is provided such that the processor compares the first and second versions of the program and selects the newer version for execution and the processor receives the newer version of the program for programming of the at least one programmable device. The system is further provided such that the programmable device processes the image data received from the camera.

In another advantageous embodiment, a method for processing image data is provided comprising the steps of coupling a camera to a camera control unit and detecting the connection of the camera to the camera control unit. The method further comprises the steps of accessing a first version of a program stored on a first storage device on the camera, accessing a second version of the program stored on a second storage device and comparing the first and second versions to determine which version is the newer version. The method still further comprises the steps of uploading the newer version to the processor, programming a programmable device based on the uploaded program and processing image data generated by the camera and transmitted to the camera control unit.

In still another advantageous embodiment, a video imaging system is provided comprising a camera having a first storage device with a first version of a program stored therein, the program including data related to the camera. The system further comprises a camera control unit coupled to the camera, the camera control unit having a programmable processing device for processing image data received from the camera and a second storage device accessible by the camera control unit having a second version of the program stored thereon. The system is provided such that the camera control unit compares the first and second versions and uploads the newer version so that the programmable processing device is programmed with the newer version program and the programmable processing device processes the image data received from the camera.

The invention and its particular features and advantages will become more apparent from the following detailed description considered with reference to the accompanying drawings.

DETAILED DESCRIPTION OF THE INVENTION

Figure 1:
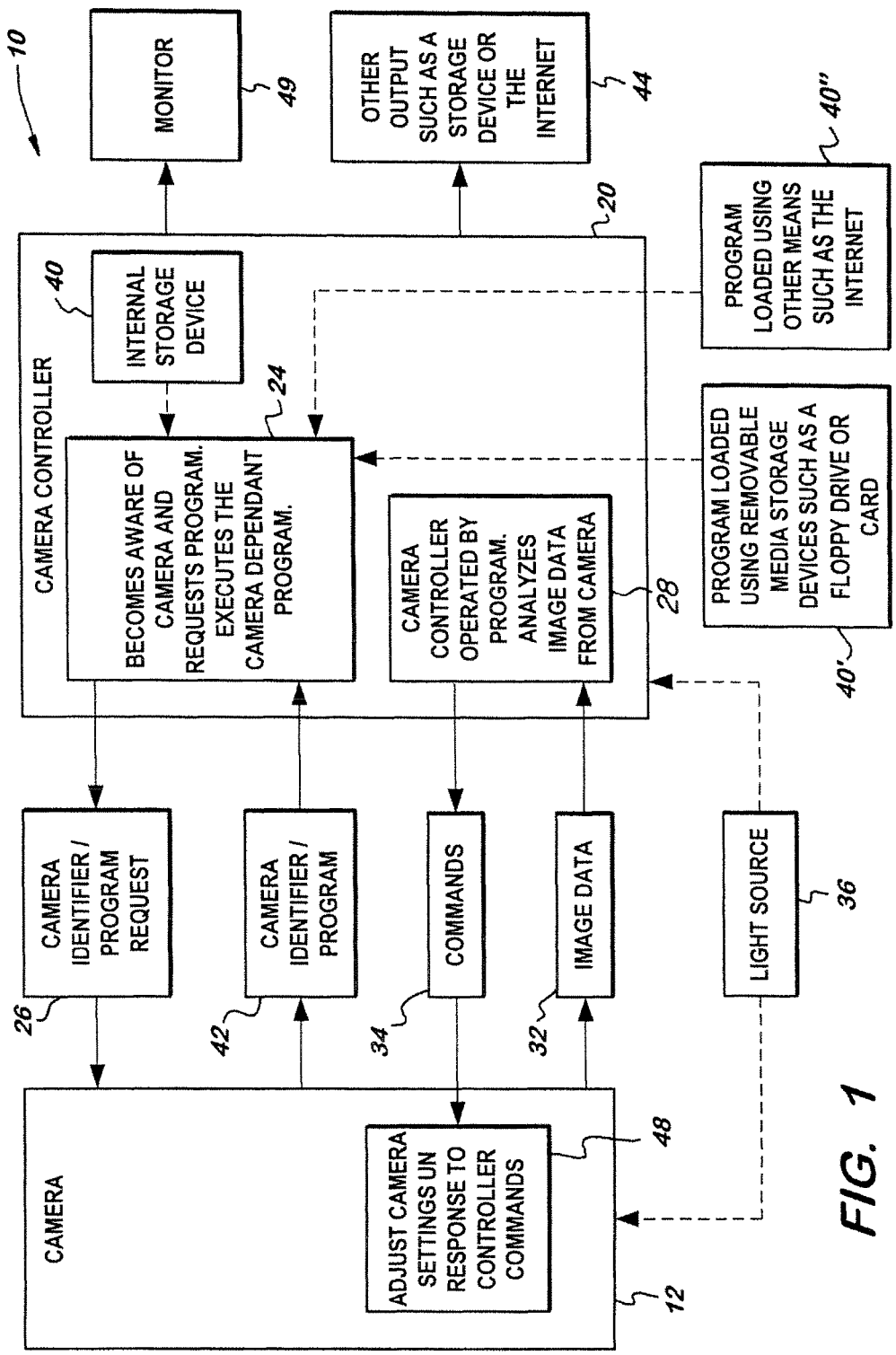
FIG. 1 is a block diagram of the system for video imaging.

FIG. 1 depicts a system 10 for video imaging, comprising a camera 12 for transmitting image data and camera control unit 20 for receiving and processing image data, particularly endoscopic video imaging. System 10 further includes storage device 40 for storing program 42 and an electronic system for determining when camera 12 is in communication with camera control unit 20 and for retrieving program 42.

Camera 12 captures image data and transmits it to camera control unit 20 to process a displayable image. Camera 12 may include one or more charge coupled devices ("CCD"), including different types of CCDs or multiple ones of a single type of CCD or may include a C-MOS device. Camera 12 may further include known cameras in the field and/or novel cameras including storage device 40 for storing program 42.

Control unit 20 is the brain of the camera. It commands camera 12 to adjust camera settings and desired image data. Control unit 20 then receives and processes the image data transmitted from camera 12. Processing image data includes transforming the digital data sent from the camera into a displayable format, such as on a monitor. Control unit 20 may also save the processed image data on a recording device for later use.

Storage device 40 includes any medium for storing applications and/or programs 42. Storage device 40 may be located internally or externally of control unit 20 and/or camera 12. In addition, storage device 40 may further a removable storage medium 40' or a remote location 40", such as an Internet location.

Control unit 20 may become aware 24 of camera 12 in any number of ways including a mechanical switch, RF, optical, electrical, or magnetic coupling, signal, or the like.

Upon becoming aware of a communication, either wired or wireless, between control unit 20 and camera 12, control unit 20 requests or receives 26 program 42 from storage device 40, 40', 40". Control unit 20 may also request or receive a camera identifier in addition to, or instead of, the request for program 42. The camera identifier provides control unit 20 with information regarding compatibility so that control unit 20 can determine whether or not it is compatible with the camera in which it is in communication. If camera 12 and control unit 20 are compatible, control unit 20 may terminate its request for program 42.

Once program 42 has been transmitted, control unit 20 executes program 42, which programs or configures control unit 20. In programming or configuring control unit 20, program 42 may overwrite an existing application. The existing application may have been for compatibility purposes between control unit 20 and a pre-existing camera. Because the pre-existing camera has been replaced with camera 12, program 42 may overwrite the existing application so that camera 12 may be compatible with control unit 20. Once programmed or configured, control unit 20 may receive and process 28 image data 32 transmitted by camera 12. Hence, control unit 20 may thereafter issue commands 34 to camera 12 to adjust 48 its optical characteristics and camera 12 may send confirmation to control unit 20 that such commands were received and/or that camera 12 will comply.

Light source 36 may be provided at camera 12 for providing light to enable a user to see images captured by camera 12. Light source 36 may also be provided at control unit 20 or a cable connecting camera 12 and control unit 20, where light is transmitted to camera 12 via fiber optic cables or other known or novel cables capable of transmitting light through a connection between camera 12 and control unit 20.

The cable used in a wired communication between camera 12 and control unit 20 may comprise a bundle of separate fibers capable of carrying data from camera to control unit and from control unit back to camera. The data transmitted through the bundle of fibers includes light to the camera, image data to the control unit, and commands to the camera. Traditionally, the cable used to transmit the vast amounts of data between camera and control unit was large and heavy because of the quantity of fibers used within the cable.

In another embodiment, a single multimode fiber cable may be provided whereby a smaller quantity of fibers may transmit as much data, and preferably more, as the bundle of separate fibers traditionally used. For example, the multimode fiber cable may include a fiber capable of transmitting data to and from a camera instead of simply transmitting data in one direction. Further, the multimode fiber cable may include a fiber capable of transmitting both image data and light.

After control unit 20 processes 28 image data 32, control unit 20 may send the processed images to a monitor 49 for display. Control unit 20 may also send the images to recording device 44, including an internal, external, or removable storage device. Recording device 44 may also include a remote location such as an Internet location. Processed image data may be sent to recording device 44 for any number of reasons including, for example, saving the images for later use or viewing.

Figure 2:
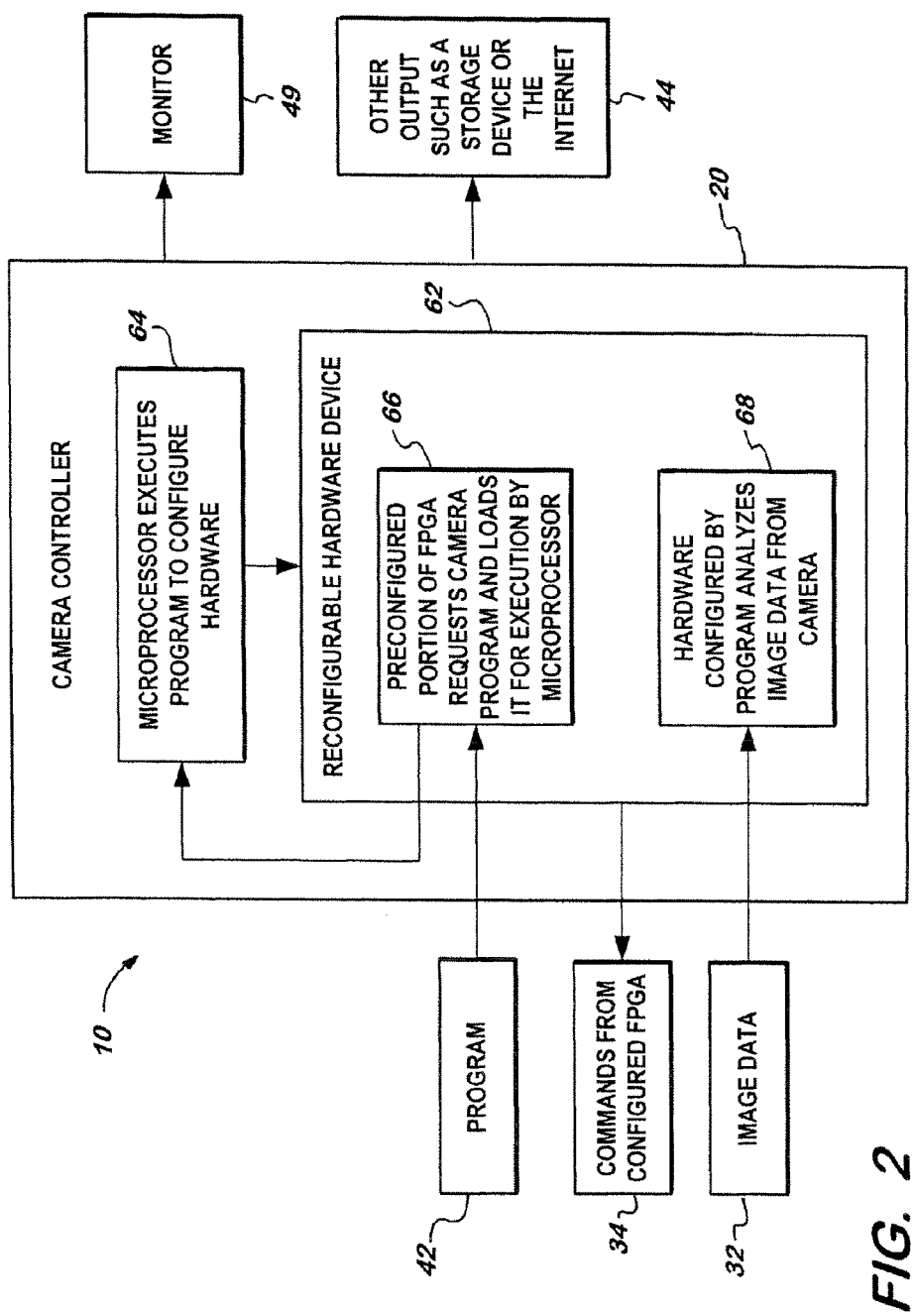
FIG. 2 is a block diagram of the camera control unit having a field programmable gate array.

FIG. 2 more specifically depicts the system 10 for video imaging comprising control unit 20, programmable device 62, and microprocessor 64. Programmable device 62 further comprises a first section 66 for requesting/receiving program 42 and a programmable second section 68 for programming or configuring control unit 20 to be compatible with camera 12.

Programmable device 62 operates as the hardware of control unit 20 for retrieving program 42 and permitting program 42 to program or configure, including overwriting, itself. First section 66 of programmable device 62 is for requesting/loading program 42. First section 66 may also, but need not, be permanently configured for requesting/loading program 42. Upon becoming aware of a communication between control unit 20 and camera 12, it is first section 66 of the camera control unit that may request program 42 from storage device 40.

Once program 42 has been received by first section 66, first section 66 loads it for execution by microprocessor 64. Microprocessor 64 executes program 42, which may be an executable or compressed file to program microprocessor 64. Execution includes opening, compiling, and/or running program 42, whereby program 42 is launched and performs the functions/operations for which program 42 was written.

Concurrent with or after execution and programming of microprocessor 64, program 42 executes on microprocessor 64 to program or configure second section 68 of field programmable device 62. Programming or configuring second section 68 includes reprogramming/overwriting second section 68 hardware. Programming or configuring second section 68 further includes replacing or overwriting an existing program thereon. In this manner, a single program 42 is downloaded to programmable device 62, which comprises a first processor program for programming of microprocessor 64 and a second device program for programming of programmable device 62. While the programmable device 62 in this embodiment is described as a field programmable gate array, it should be noted that the programmable device 62 may comprises a soft configurable device such as, for example, a microprocessor or a Digital Signal Processor (DSP).

Once second section 68 is programmed or configured by program 42, control unit 20 is desirably compatible with camera 12. Hence, control unit 20 may issue commands to camera 12 and process image data 32 transmitted from camera 12. Control unit 20 may further send the processed image data to a displayable medium, such as a monitor, or to a second storage device, such as recording device 44 or an Internet location. It is further contemplated that programmable device 62 may not be provided with a preconfigured section but may be entirely programmable or configurable and that the program 42 (including both the processor and device programs) may be sent directly to microprocessor 64.

Figure 3:
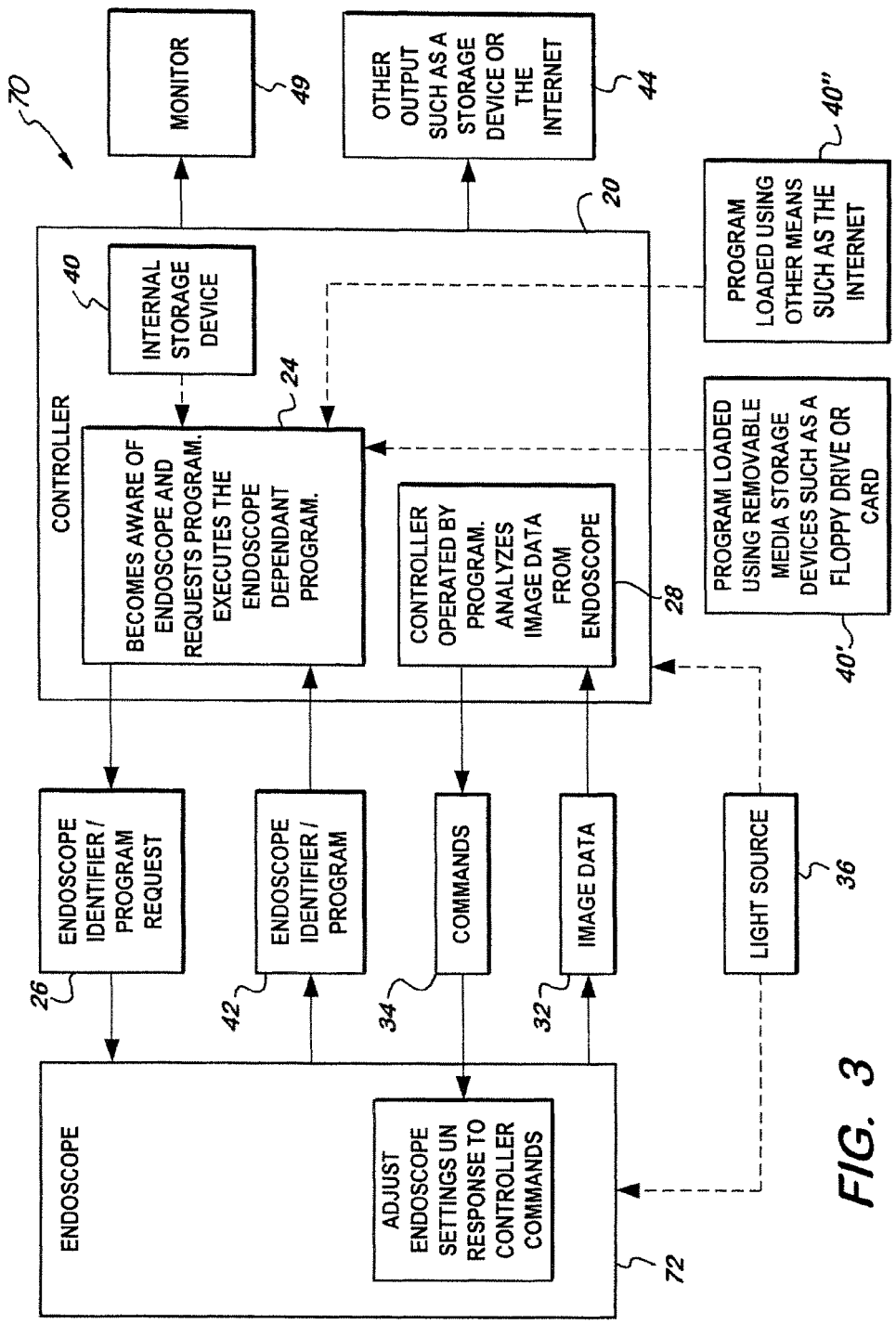
FIG. 3 is a block diagram of an endoscopic video imaging system.

FIG. 3 depicts another embodiment for a system 70 for video imaging comprising an endoscope 72 for transmitting image data 32, control unit 20 for receiving and processing image data, storage device 40, 40', 40" for storing program 42, and an electronic system for determining when endoscope 72 is in communication with control unit 20 and for retrieving program 42.

Endoscope 72 operates in the same manner as camera 12, as described in FIG. 1, to capture and transmit image data 32 to control unit 20. Endoscope 72 may further comprise one or more CCDs, including different types of CCDs or multiple ones of a single type of CCD or a C-MOS device. Endoscope 72 may also include storage device 40 for storing program 42. Endoscope 72 merely replaces camera 12 in system 70 for video imaging.

Figure 4:
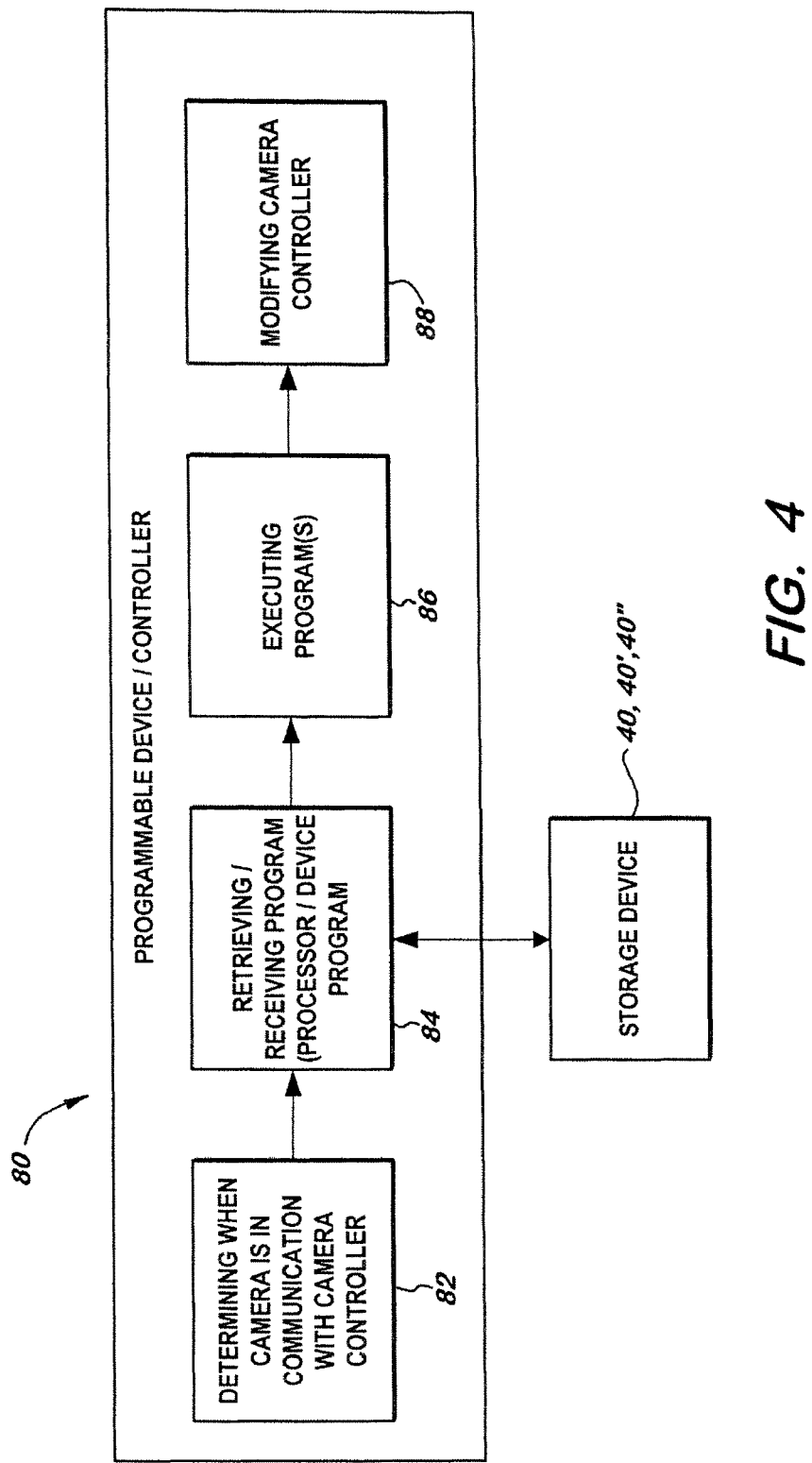
FIG. 4 is a block diagram of a method for video imaging.

FIG. 4 depicts a block diagram of a method 80 for video imaging comprising the steps of determining 82 when camera 12 is in communication with control unit 20, retrieving 84 program(s) 42 from storage device 40, 40', 40", executing 86 program(s) 42, and modifying or programming 88 control unit 20 to enable control unit 20 to be compatible with camera 12.

An electronic system determines 82 when control unit 20 and camera 12 are in communication with each other. The electronic system may determine 82 the communication through any number of ways including a mechanical switch, RF (e.g. RFID), optical, electrical, or magnetic coupling (e.g. RuBee, a bidirectional, on-demand, peer-to-peer, radiating, transceiver protocol operating at wavelengths below 450 Khz), signal, or the like.

Upon determining 82 communication between camera 12 and control unit 20, control unit 20 retrieves/receives 84 program(s) 42 from storage device 40, which includes any medium for storing applications and/or program(s) 42.

After program(s) 42 has been retrieved/received 84, control unit 20 executes 86 program(s) 42. Executing 86 program(s) 42 includes opening, compiling, and/or running program(s) 42, whereby program 42 is launched and performs the functions/operations for which program 42 was written including, for example, running a first processor program to program the processor and then running a second device program to program the programmable device.

Concurrent with or after executing 86 program(s) 42, method includes programming or configuring 88 control unit 20 to enable control unit 20 to process image data 32 transmitted from camera 12. Programming or configuring 88 control unit 20 may include reprogramming/overwriting an existing application on control unit 20.

Once programmed, control unit 20 may thereafter issue commands to camera 12 and process image data 32 transmitted from camera 12. Control unit 20 may further send the processed image data to a displayable medium, such as a monitor, or to a second storage device, such as recording device 44 or an Internet location.

Figure 5:
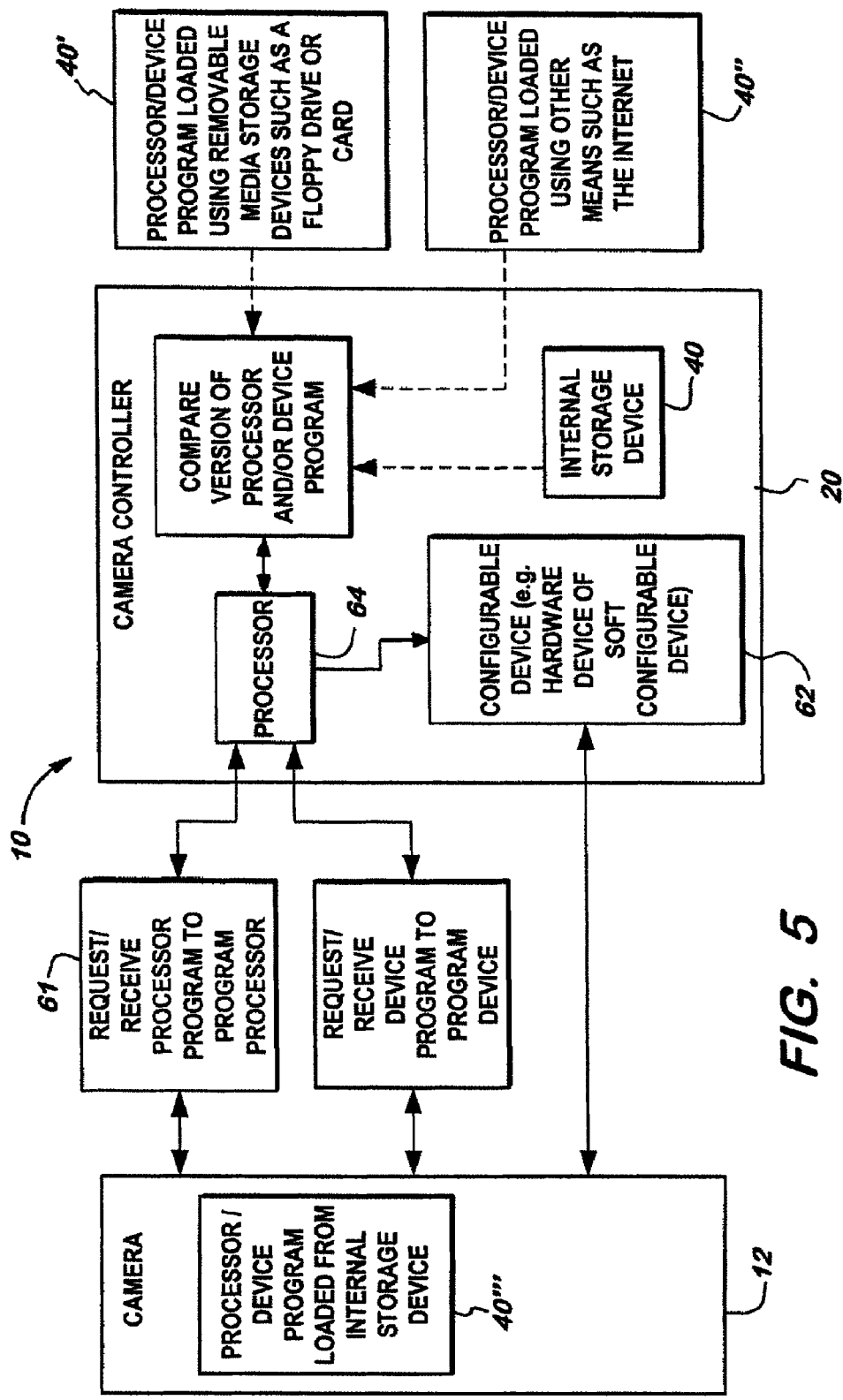
FIG. 5 is a block diagram of one advantageous embodiment of the present invention according to FIG. 1.

Referring now to FIG. 5, a block diagram according to the system of FIG. 1 is illustrated showing system 10 for video imaging, comprising a camera 12 for transmitting image data and camera control unit 20 for receiving and processing image data.

Camera 12 includes an internal storage device 40''', from which program(s) 42 may be loaded to camera control unit 20. Initially, camera control unit becomes aware that camera 12 is connected thereto and requests processor program 61 from camera 12. The processor program is further available from storage device 40, 40', 40'' such that, processor 64 compares the various available versions from the various storage devices 40, 40', 40'', 40''' and uses the newest version. In addition, it is contemplated that the version on storage device 40''' may automatically be updated with a newer version available to processor 64. Once the processor is programmed, processor may request and/or receive device program 63. Again, the processor 64 may automatically select the newest version available to processor 64 from the various storage devices 40, 40', 40'', 40''' and uses the newest version; as well as automatically update the version on the camera to reflect the newest version.

While the steps of loading the processor program and device program have been described as being performed in two distinct steps, it is contemplated that a single program 42 may be downloaded and executed, the program 42 including, for example, both the processor program and the device program as well as other information/data/programs for the control unit and/or camera.

Once the processor 64 is programmed, the programmable device 62 is programmed to be compatible with the connected camera 12. In addition, while the processor 64 is illustrated separate from programmable device 62, it is contemplated that both devices may advantageously be provided as a single physical device and/or chip to minimize space and/or interconnections.

Although the invention has been described with reference to a particular arrangement of parts, features, and the like, these are not intended to exhaust all possible arrangements or features, and indeed many other modifications and variations will be ascertainable to those of skill in the art.

What is claimed is:

1. A video imaging system, comprising:
a camera generating image data;
said camera having a storage, which has camera identifying data stored thereon;
a camera control unit coupled to said camera;
said camera control unit receiving the image data, wherein said camera control unit includes:
a processor; and
at least one configurable device;
said processor having a processor program executing on said processor and receiving a device program corresponding to the camera identifying data, wherein said received device program executes on said camera control unit and programs said at least one configurable hardware device;
said configurable hardware device processing said image data received from said camera.

2. The video imaging system according to claim 1 wherein said device program enables said camera control unit to issue a command to said camera to adjust an operating characteristic of the camera.

3. The video imaging system according to claim 2 wherein said camera sends confirmation to said camera control unit that the command was received.

4. The video imaging system according to claim 1 wherein said at least one configurable hardware device is selected from the group consisting of: field programmable gate arrays, microprocessors and digital signal processors.

5. The video imaging system according to claim 1 wherein said processor is selected from the group consisting of digital signal processors, microprocessors and microcontrollers.

6. The video imaging system according to claim 1 wherein said processor and said configurable hardware device are packaged as a single integrated device.

7. The video imaging system according to claim 1 further comprising software executing on said camera control unit for determining when said camera is in communication with said camera control unit.

8. The video imaging system according to claim 7 further comprising an image storage device and image data is stored on said image storage device.

9. The video imaging system according to claim 8 wherein the image data stored on said image storage device is processed image data.

10. A method for processing image data comprising the steps of:
coupling a camera to a camera control unit;
coupling a storage to the camera;
saving camera identifying data on the storage;
providing a processor in the camera control unit, the processor having a processor program running thereon;
providing at least one configurable device in the camera control unit;

coupling the processor to the at least one configurable device;

transmitting the camera identifying data to the processor;

receiving a device program on the processor;

programming, via the received device program executing on the camera control unit, the at least one configurable device;

generating image data with the camera;

transmitting the image data to the at least one configurable device; and processing image data with the at least one configurable device.

11. The method according to claim 10 further comprising the step of issuing a command via the device program to the camera to adjust an operating characteristic of the camera.

12. The method according to claim 11 further comprising the steps of:

sending a command is to the camera; and sending a confirmation to the camera control unit that a command was received.

13. The method according to claim 10 further comprising the step of determining when the camera is in communication with the camera control unit.

14. The method according to claim 13 further comprising the steps of providing an image storage device and storing the image data on the image storage device.

15. The method according to claim 14 wherein the image data stored on the image storage device is processed image data.

* * * * *